United States Patent [19]

Flesch

[11] Patent Number: 5,681,263
[45] Date of Patent: Oct. 28, 1997

[54] ENDOSCOPE FOR ULTRASONIC ECHOGRAPHY

[75] Inventor: Aimé Flesch, Andresy, France

[73] Assignee: Vermon, France

[21] Appl. No.: 391,021

[22] Filed: Feb. 21, 1995

[30] Foreign Application Priority Data

Feb. 25, 1994 [FR] France ................. 94 02211

[51] Int. Cl.⁶ .................................... A61B 1/008
[52] U.S. Cl. ................ 600/141; 600/149; 600/139; 128/662.06
[58] Field of Search ................. 600/141, 144, 600/149, 150, 139, 148; 604/280, 95; 128/772, 658, 657, 662.06, 660.01

[56] References Cited

U.S. PATENT DOCUMENTS

| | | |
|---|---|---|
| 4,655,257 | 4/1987 | Iwashita . |
| 4,787,369 | 11/1988 | Allred, III et al. . |
| 4,796,607 | 1/1989 | Allred, III et al. ........... 600/141 |
| 5,191,890 | 3/1993 | Hileman ............... 128/662.06 |
| 5,271,381 | 12/1993 | Ailinger et al. . |
| 5,331,948 | 7/1994 | Utsumi et al. ............ 600/148 |
| 5,448,989 | 9/1995 | Heckele .................. 600/149 |

FOREIGN PATENT DOCUMENTS

| | | |
|---|---|---|
| 0165718 | 5/1985 | European Pat. Off. . |
| 4222121 | 9/1993 | Germany . |
| 9218054 | 10/1992 | WIPO . |

*Primary Examiner*—Richard J. Apley
*Assistant Examiner*—John P. Leubecker
*Attorney, Agent, or Firm*—Larson and Taylor

[57] ABSTRACT

The endoscope comprises a probe for ultrasound echography, a manual control housing (12) carrying adjustment members that are connected by cables to the base, a tube (50) fixed to the housing and having cables passing therealong, and a mechanical coupler enabling the base to be given a position that is angularly adjustable. The mechanical coupler has a plurality of links connected in series that are capable of tilting relative to one another. The links are maintained pressed mutually against one another solely by cables for putting them under resilient tension from the housing. They are all of the same shape and the shape is such as to allow each link to tilt in at least one direction from a position in which the coupler is essentially straight.

8 Claims, 4 Drawing Sheets

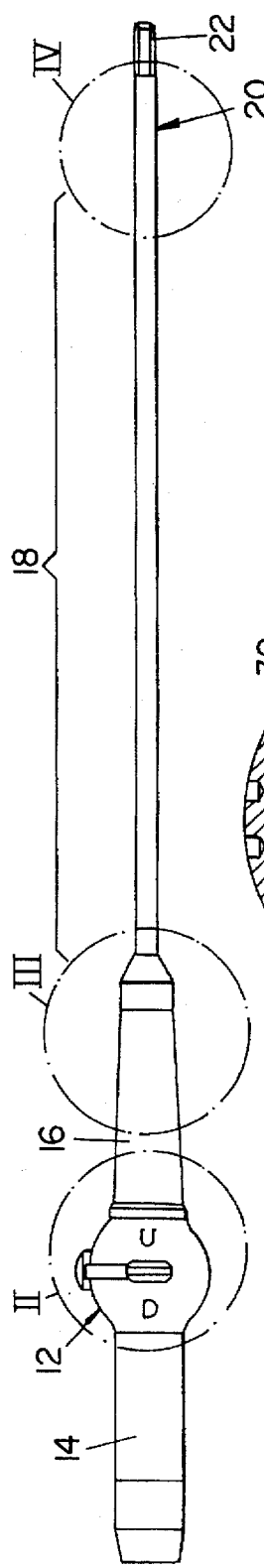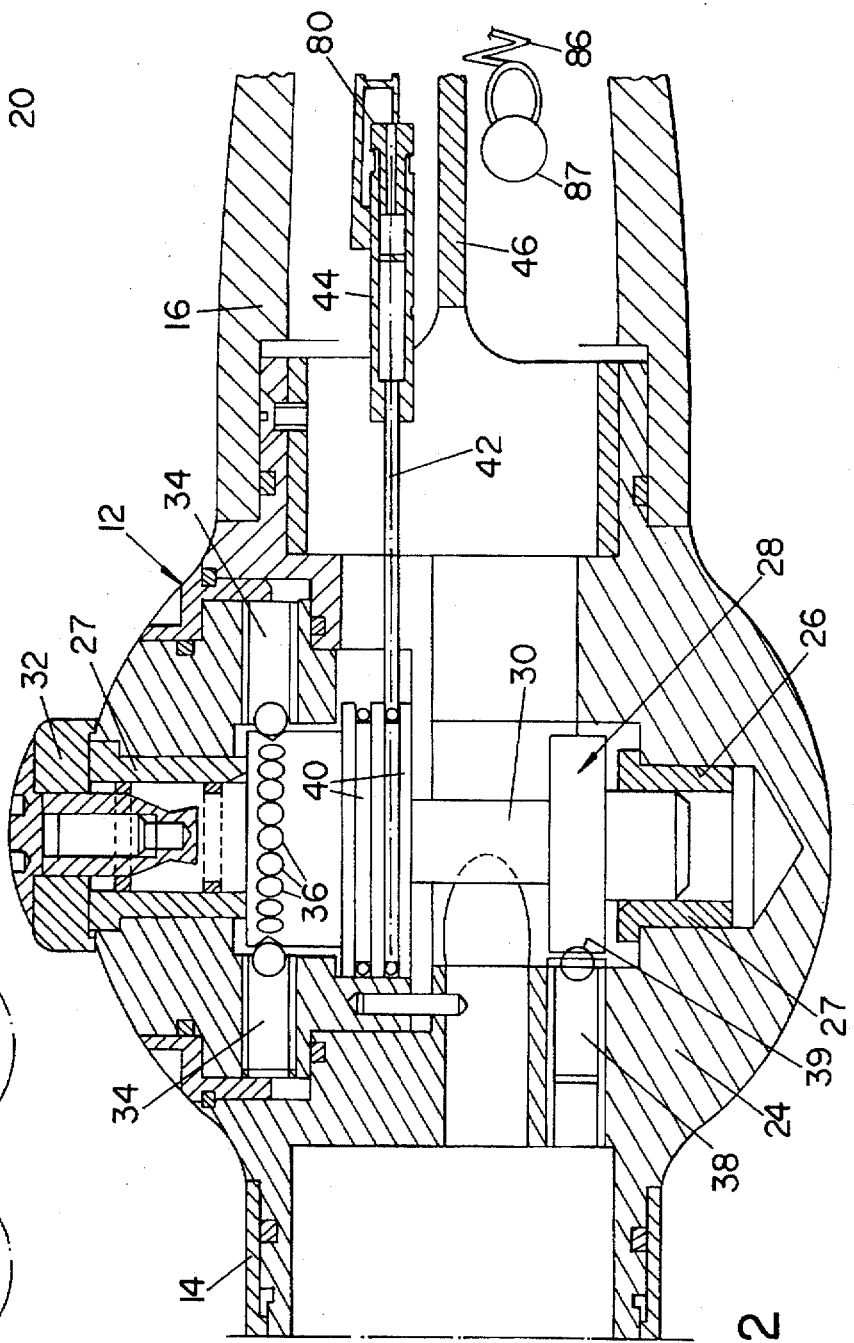
FIG. 1
FIG. 2

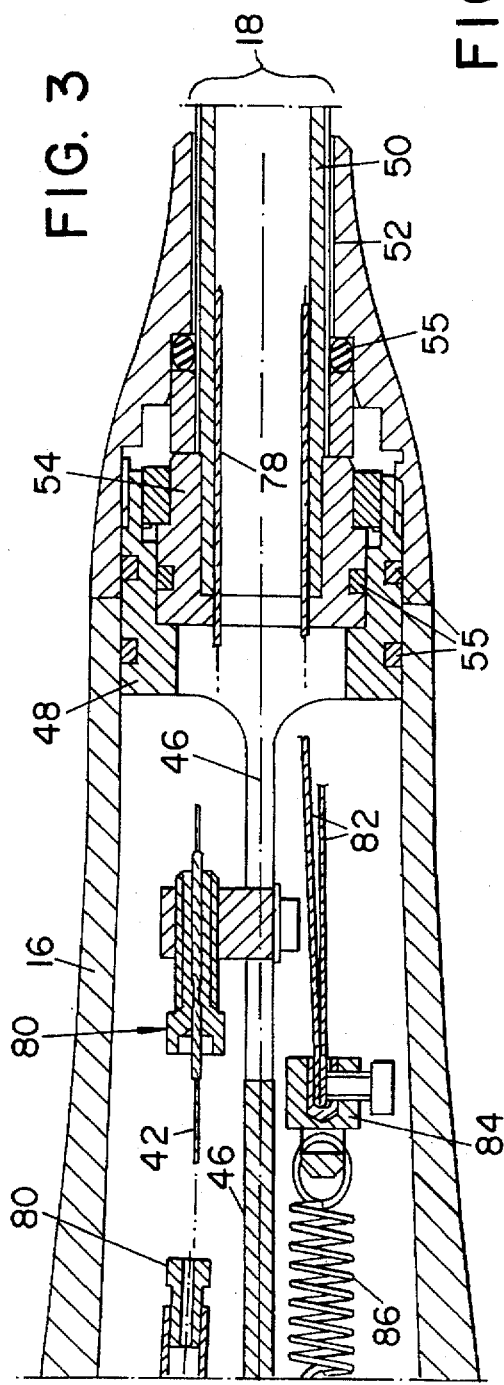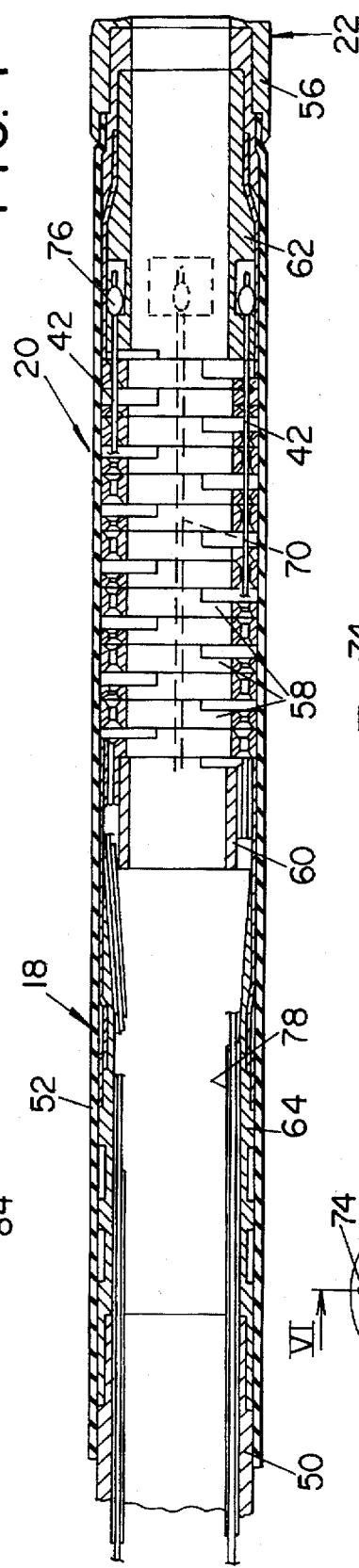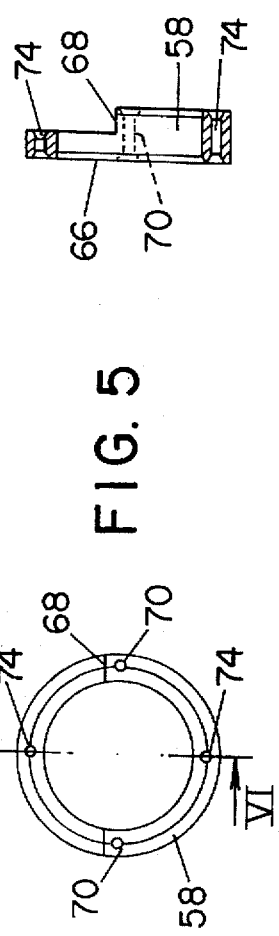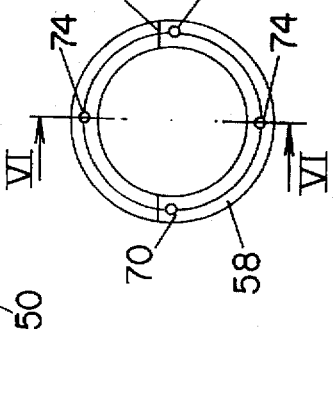

ENDOSCOPE FOR ULTRASONIC ECHOGRAPHY

BACKGROUND OF THE INVENTION

The present invention relates to endoscopes and more particularly to those designed for medical use, and including a scanning ultrasound probe instead of, or in addition to, an optical system. A major application thereof lies in echographic endoscopes, such as those used for coelioscopy and gastroscopy.

It is desirable for such endoscopes to have properties that are difficult to reconcile. Attempts have already been made to give them a physical structure enabling them to be inserted and withdrawn without difficulty and making it possible to steer the terminal probes thereof in such a manner as to bring them to the location to be explored, to be pressed against an organ, and/or to change the orientation of the plane in which scanning is performed. For that purpose, an endoscope has already been proposed that comprises:

- an ultrasound echography probe having a strip of ultrasound transducers carried by a base that defines a reception cavity for conductors that feed excitation signals to the transducers and that return echo signals, thereby enabling ultrasonic scanning to be performed electronically that is linear, angular, or panoramic;
- a manual control housing carrying adjustment members connected by adjustment cables to the base;
- a tube fixed to the housing and having the conductors and the adjustment cables passing therethrough; and
- a mechanical coupler connecting the tube to the base of the probe and controllable by means of the adjustment members to impart an adjustable angular position to the base in at least one steering plane, the mechanical coupler comprising a plurality of links mounted in series and capable of tilting relative to one another in the steering plane under drive from the adjustment cables.

An endoscope of that type is described in U.S. Pat. No. 5,191,890. The possibility of tilting the links relative to one another is provided by hinges interconnecting them. Consequently, this option is obtained at the expense of safety. If a hinge were to break or to jam, then there would be a danger of the coupler being blocked in a state that prevents it from being extracted.

The invention seeks in particular to reduce this risk to a great extent. For this purpose, the invention proposes an endoscope of the type defined above, in which said links:

- are held in mutual engagement solely by the cables which are put under resilient tension from the housing; and
- are of a shape such as to enable each link to tilt in at least one direction starting from a position in which the coupler is substantially straight.

Advantageously, the links are constituted by rings, so as to define a central passage for signal-conveying conductors (high tension pulses for energizing the transducers of the strip, and low level echo signals as delivered by the transducers). This structure protects the conductors. In general, the cables include two crossed pairs of diametrically opposite cables, the cables of one pair constituting axial cables while the cables of the other pair constitute cables for steering. The holes via which the cables pass through the rings are advantageously chamfered conically so as to facilitate sliding of the cables during steering control operations. In general, the angle at the apex of such a cone is about 60°.

In an endoscope constituting a first embodiment of the invention, and capable of steering the probe in a single plane only, each of the links has a flat face and another face made up of two segments parallel to the first face and interconnected by a shoulder that is parallel to the axis, the segment corresponding to the greater thickness occupying more than half of the second face. In which case, two successive links are mounted head to tail. The minimum radius of curvature that the coupler can take up depends on the size of the shoulder.

An endoscope constituting a second embodiment which makes steering possible in all planes that contain the axis of the coupler when the coupler is straight includes links each of which is constituted by an annular disk having a first pair of two diametrically-opposite projections on one face and having a second pair of two diametrically-opposite projections on its opposite face but at 90° to the first pair, with successive adjacent links facing in opposite directions.

Other characteristics that are advantageously used in combination with the above characteristics, but that could be used independently, appear more clearly on reading the following description of particular embodiments given by way of non-limiting examples. The description refers to the accompanying drawings.

BRIEF DESCRIPTION OF THE DRAWINGS

FIG. 1 is an overall elevation view of an endoscope that can be implemented in application of the invention;

FIGS. 2, 3, and 4 are fragmentary views on a larger scale and in section on a plane that includes the axis of the endoscope, showing portions marked II, III, and IV in FIG. 1, and constituting a first embodiment of the invention;

FIGS. 5 and 6 are respectively an end view and a section on plane VI of FIG. 5 showing one of the links shown in FIG. 4;

DETAILED DESCRIPTION

Figure 7:
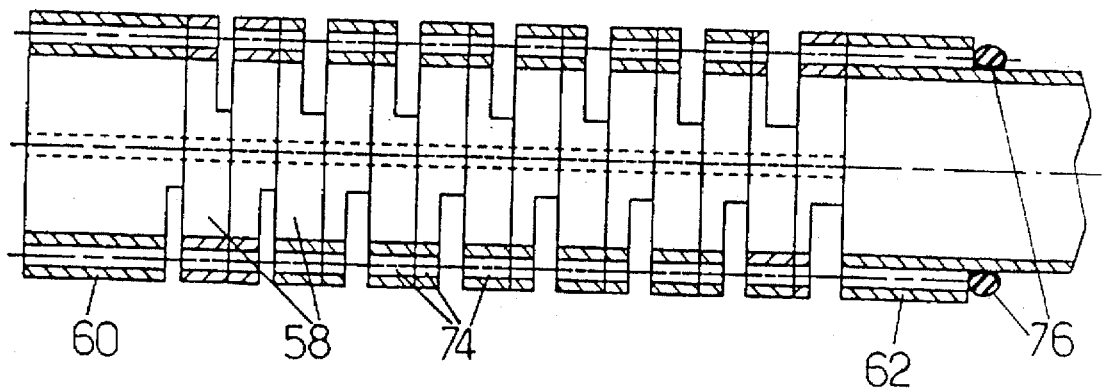
FIGS. 7 and 8 are cross sections on a plane including the axis and show the relative disposition of the links of the coupler shown in FIG. 2, respectively when the coupler is straight and when it presents maximum curvature.
Figure 8:
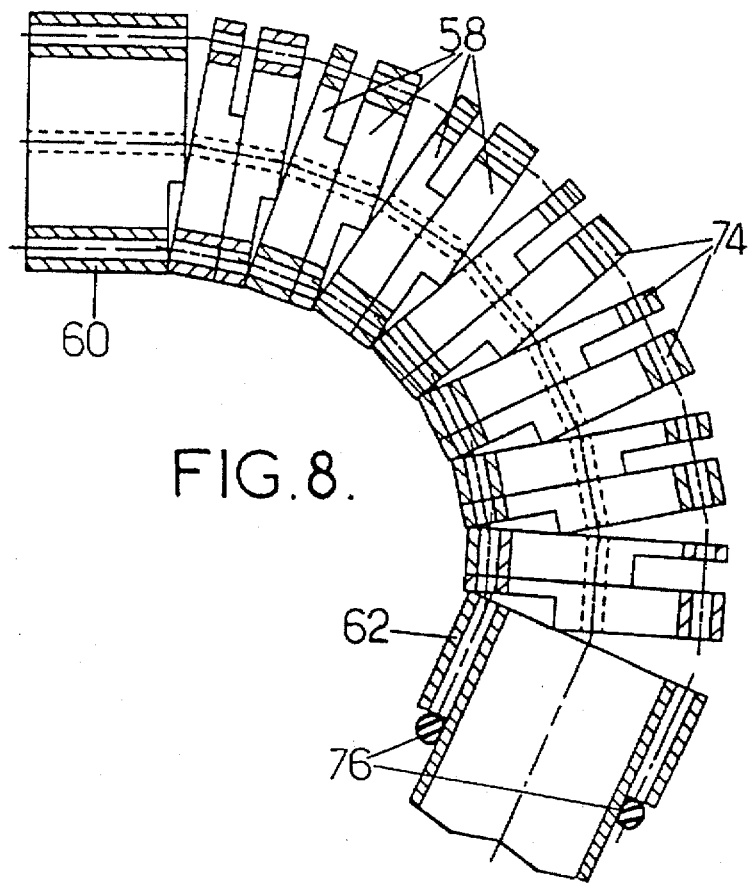

The endoscope shown in FIG. 1 is designed for medical echography, and it is particularly suitable for use in coelioscopy, even though it is also suitable for other applications, such as exploring the digestive tract, given the diameter with which it can be made. The mechanical components of the endoscope are also suitable for optical endoscopy; it is suitable for steering a terminal probe in one plane, only.

The endoscope shown in FIG. 1 may be considered as comprising:

- a control box 12 designed to remain outside the organs to be explored, provided with a proximal endpiece 16 and with a proximal endpiece 14 through which there pass conductors (not shown) for connection with electronics associated with the device;
- a sealed tubular assembly 18;
- a steering coupler 20; and
- a probe 22 that can be steered by means of the coupler 20.

The probe may have any of numerous well-known structures. For example, it may be a curved echographic probe having electronic scanning and focusing of the kind described in document U.S. Pat. No. 4,605,009, optionally associated with an optical endoscope described in the same document, to which reference may be made.

When the endoscope is intended for medical applications, it is made of materials suitable for being sterilized. In particular, if provision is made for sterilization by the application of heat, materials should be used that are capable of withstanding a temperature of about 400° C. without deforming, e.g. stainless steel for the cables, synthetic resins for the insulators, and high temperature resisting elastomers for the flexible portions.

The control housing 12 shown in FIGS. 2 and 3 comprises a body 24 provided with two extensions having endpieces 14 and 16 engaged and bonded thereon. A blind hole 26 formed in the body contains rings 27 within which there rotates a part 30 belonging to rotary equipment 28 also including a control knob 32. Resilient ball latches 34 co-operate with indentations 36 formed in the rotary part 30 to hold it in the position in which it is placed manually by using the knob 32. An additional ball latch 38 co-operates with a single indentation 39 placed in such a manner as to ensure that the latch is engaged when the coupler 20 is straight. The resilient latch 38 holds the probe in its straight state as shown in FIG. 1 with sufficient strength to avoid any risk of bending under the action of bending stresses during insertion or withdrawal.

The rotary part 30 has two circumferential grooves 40 for winding control cables 42 which are described further below. The cables pass through guides 44 which, in the embodiment shown, are placed on the same side of a partition 46. Resilient means for tensioning the cables (described below) may be placed in the empty volume situated on the other side of the partition. In the embodiment of FIGS. 2 and 3, the housing is made up of a plurality of parts that are assembled by means of screws or by mutual engagement and adhesive: other constructions would also be possible.

The sealed tubular assembly 18 is secured to the proximal endpiece 16 of the housing 12. In the embodiment shown in FIGS. 3 and 4, the assembly is secured to a ring 48, itself secured to the end of the partition 46, and having a sliding fit in the proximal endpiece 16. The assembly 18 includes a structural inner tube 50 which, depending on the intended application, is either a rigid tube (e.g. made of stainless steel) or else a tube of synthetic material that has a certain amount of flexibility, but that is not steerable. A sealing sleeve 52 is threaded over the inner tube 50 and slidable thereon except at its ends. In the example shown, the end of the sleeve adjacent to the housing is clamped on the inner tube 50 by a clamping ring 54. The sleeve is made of an elastomer that is flexible and stretchable, e.g. being made of neoprene and generally being designed to remain leakproof under a pressure difference of several bars. Sealing rings 55 prevent leaks from the inside of the housing and from the inside of the sleeve to the outside. The end fixings of the sleeve 52 may be designed to keep it under a small amount of tension when the endoscope is straight. This ensures that the sleeve is in no danger of presenting creases on the insides of bends when the probe is steered.

The coupler 20 (FIG. 4) connects the sealed tubular assembly to a base 56 that belongs to the probe. It comprises a stack of links 58 bearing against one another and bearing against two end links 60 and 62 at opposite ends of the stack. The proximal link 60 is fixed to the inner tube 50 by a bush 64 having the sleeve 52 passing thereover. The distal link 62 has an extension that is received within and bonded to the base 56. The sleeve 52 covers the stack and is capable of sliding thereover, and its end is fixed in sealed manner to the base 56.

When the endoscope is designed to allow steering in a single plane only, then the links may have the structure shown in FIGS. 5 to 8. Various spring arrangements are possible including that disclosed in U.S. Pat. No. 4,655,257 to IWASHITA. Each regular link 58 is in the form of a ring that has a flat first face 66 and an opposite face made up of two segments parallel to the first face and interconnected by a shoulder 68 parallel to the axis (FIG. 6). The segment corresponding to the greater thickness occupies more than half of the second face, often 55% to 70% thereof. Two successive links are mounted head to tail. It is optional whether the links 60 and 62 present a stepped face facing the stack. The links are in the form of rings so as to define a tubular space through which conductors can pass to the probe. The links are made of a material commonly used for making smooth bearings, e.g. bronze. Depending on whether or not it is desired for the curvature of the coupler, when curved, to be constant or otherwise, the links are all of the same thickness, or else they are of differing thicknesses.

The links are held pressed against one another by small diameter metal cables resiliently tensioned from the housing. The cables comprise two pairs which are placed in orthogonal planes inside the coupler. In the embodiment of FIGS. 2 to 8, the cables 82 of one of the pairs pass through holes 70 having end conical chamfers and situated in a plane parallel to the shoulders 68, these cables constituting axis cables. The cables 42 in the other pair are situated in a plane that is orthogonal to the plane of the cables in the first pair, and likewise pass through holes 74 in the links, which holes are provided with end chamfers. The cables are made up of a plurality of strands in order to be flexible, and may have the disposition shown in FIGS. 3 and 4.

By way of example, the control cables 42 may each have one end retained in a groove of the distal link 62 by brazing 76, each cable passing through a sheath 78 pressed against the inside face of the tube 50, penetrating into the endpiece 16 through the ring 48, passing into guides 80 that make it possible optionally to adjust tension, and finally being wound in the grooves 40.

The axial cables 82 may be connected to each other. They may also be contained in sheaths inside the tube 50. Their ends are held captive in a clamp 84 secured to a traction spring 86 which is itself anchored on a screw 87 fixed to the endpiece 16.

Figure 9:
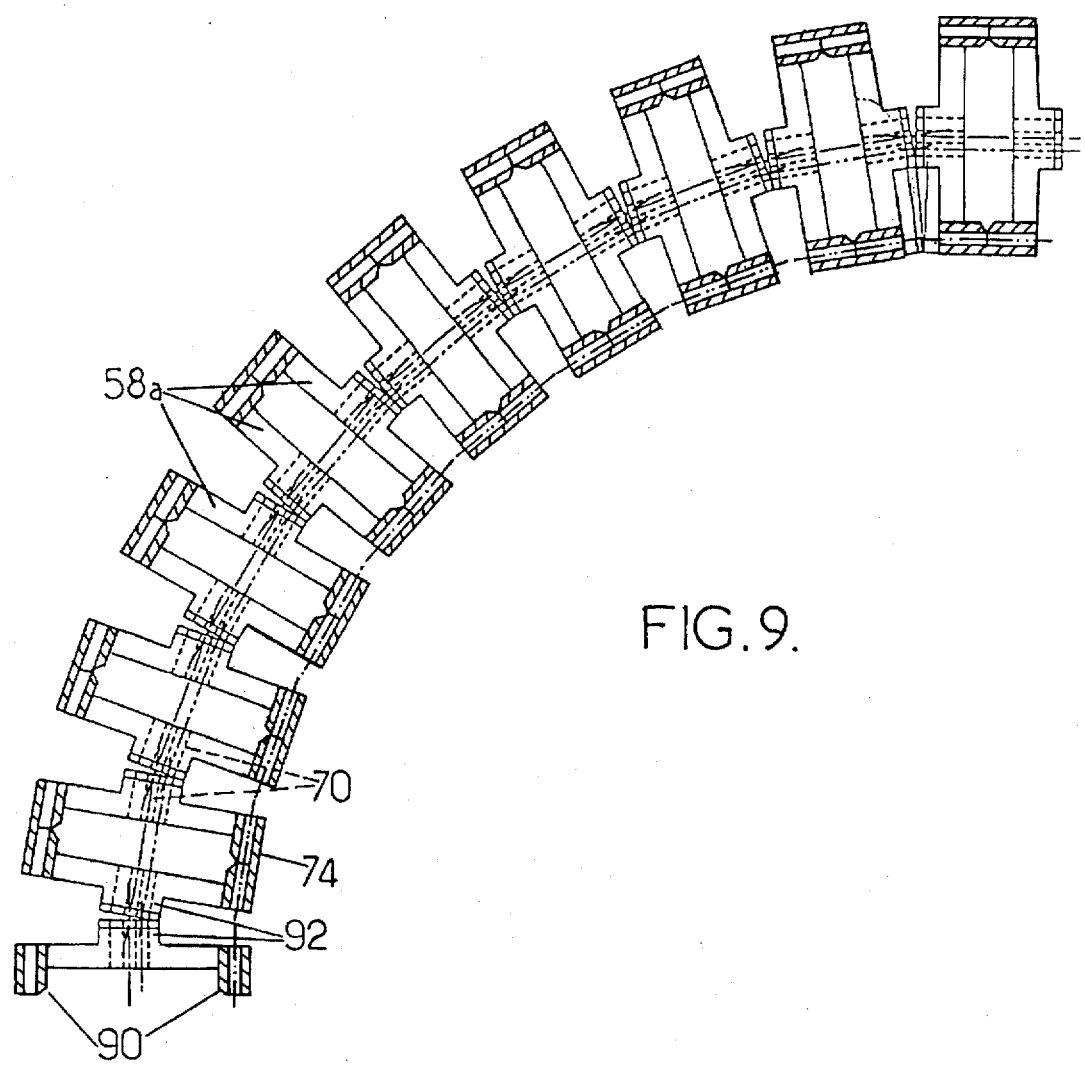
FIG. 9 is similar to FIG. 8 and shows the links of a device constituting another embodiment of the invention that enables the coupler to be curved in a plurality of different planes.

In another embodiment, the endoscope is designed to allow the probe to swing in all planes that contain the general axis of the endoscope. Under such circumstances, the links of the coupler may have the structure that is shown in FIG. 9. In this case, each link 58a is constituted by an annular disk having a first pair of two diametrically-opposite projections 90 on one face and having a second pair of two projections 92 on a second face, which projections are likewise diametrically-opposite, but on a diameter that is at 90° to the diameter on which the projections of the first pair are in alignment. Successive adjacent links thus face in opposite directions. In the stack, contact takes place first via two pairs of projections 92, then via two pairs of projections 90, and so on.

Under such circumstances, two rotating equipments may be provided in the housing. One serves to control cables passing through holes 74 while the other serves to control cables passing though holes 70. When only one of the sets of cables is actuated, it serves to curve the coupler in a plane that contains the axis of one of the sets of holes (the set of holes 74 in the example shown in FIG. 9). The cables passing through these holes 74 then constitute control cables while the others constitute axis cables. Simultaneous action on both rotary equipments enables the coupler to be curved in any plane.

In this embodiment, the overall length of each pair is liable to change so resilient means for maintaining tension are necessary on both pairs of cables.

By way of example, it may be mentioned that an endoscope has been made having fourteen regular links 58 and an outside diameter of less than 10 mm, and it allows the probe to be steered through an angle of ±113°. The axis and control cables may be seven-strand cables with a diameter of 0.7 mm. Electrical connections between the probe and the outside may be provided by individual coaxial cables comprising, from the inside towards the outside: a multi-strand conductor, a dielectric, helical shielding, and an outer sheath whose diameter does not exceed 0.35 mm. In order to limit the number of elements running along the endoscope, a plurality of coaxial cables may be grouped together in the form of a bundle having a diameter of a few millimeters, and containing up to sixty-four coaxial cables, all contained in a common shielding sheath. As shown in FIGS. 2, 3, and 4, the housing, the sealed tubular assembly, and the coupler leave a large amount of empty space for passing the coaxial cables.

Figure 10:
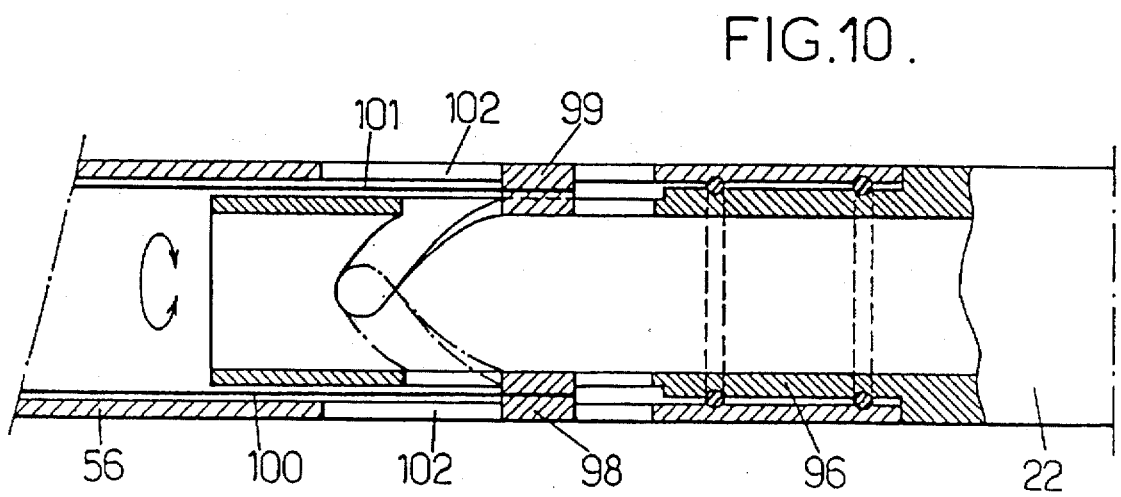
FIG. 10 is a theoretical diagram in section on a plane including the axis of the probe, showing a mechanism that enables the probe to be rotated

The endoscope may also be designed so as to make it possible not only to steer the probe in a plane containing the general axis of the endoscope, but also to cause it to revolve about said axis. Under such circumstances, the probe 22 is connected to base 56 via a bearing 96 (e.g. a smooth bearing or a ball bearing). Means for driving the probe in rotation relative to the base are provided and are suitable for being controlled mechanically from the housing. In the example shown in FIG. 10, they comprise two keys 98 and 99 that can be pulled towards the housing by respective cables 100 and 101. Each of these keys slidably engages simultaneously in a longitudinal rectilinear groove 102 in the base and in an oblique groove 104 in a tubular extension of the probe. The grooves 104 are oppositely-handed. Thus, by pulling on one of the cables, the probe is caused to rotate in one direction, with the key fixed to the other cable then being free to move forwards. Pulling on the other cable causes the probe to rotate in the opposite direction.

I claim:

1. An endoscope comprising:
   an ultrasound echography probe having a base and a strip of ultrasound transducers carried out by said base;
   a manual control housing and manual adjustment members carried by said housing;
   a tube fixed to said housing and projecting in a distal direction from said housing;
   a mechanical coupler connecting said tube to said base of said probe and controllable by means of said adjustment members, said mechanical coupler comprising a plurality of ring-shaped links mounted in series, of such a shape as to enable each said link to tilt in at least one direction with respect to the adjacent said link, starting from a position in which the coupler is substantially straight;
   a plurality of cables connecting said adjustment members and said base, located along and within said tube and said mechanical coupler, said links being held in mutual engagement solely by said cables and some of said cables being put under tension by resilient means in said housing; and
   a plurality of electrical conductors connected to said strip to feed excitation signals to said transducers and to return echo signals therefrom, said electrical conductors being connected to electronic means for delivering said excitation signals of such a nature to cause ultrasonic scanning electronically, wherein each of said links has a flat face and another face made up of two segments parallel to the flat face and interconnected via shoulders parallel to the axis, the segment corresponding to the greater thickness occupying more than half of said another face, successive adjacent links being mounted head to tail.

2. An endoscope according to claim 1, wherein each of said ring-shaped links is formed with two mutually crossed pairs of diametrically opposed holes, a first of said pairs of said holes receives a first pair of said cables which define a plane of symetry and is kept under tension by spring means placed in the housing, and another pair of said cables are received in the other said pairs of said holes and is connected to said adjustment members.

3. An endoscope according to claim 1, wherein said strip is connected to said base for rotation about a longitudinal axis, further comprising means for driving said strip in rotation from said housing.

4. An endoscope according to claim 3, wherein said means for driving the strip in rotation relative to the base comprise two keys connected to the means for driving in said housing by respective pulling cables, each of said keys slidably engaging simultaneously in one of two longitudinal rectilinear grooves in the base and in one of two oblique grooves in a tubular extension of said strip, the two oblique grooves being oppositely-handed.

5. An endoscope comprising:
   an ultrasound echography probe having a base and a strip of ultrasound transducers carried by said base;
   a manual control housing and manual adjustment members carried by said housing;
   a tube fixed to said housing and projecting in a distal direction from said housing;
   a mechanical coupler connecting said tube to said base of said probe and controllable by means of the adjustment members, said mechanical coupler comprising a plurality of ring-shaped links mounted in series, of such a shape as to enable each said link to tilt in only one direction with respect to the adjacent said link, starting from a position in which the coupler is substantially straight;
   a plurality of cables connecting said adjustment members and said base, located along and within said tube and said mechanical coupler, said links being held in mutual engagement solely by some of said cables which are put under tension by resilient means in said housing; and
   a plurality of electrical conductors connected to said strip to feed excitation signals to said transducers and to return echo signals therefrom, said electrical conductors being connected to electronic means for delivering said excitation signal of such a nature to cause ultrasonic scanning electronically;
   wherein each of said links has a flat face and another face made up of two segments parallel to the flat face and interconnected via a shoulder parallel to the axis, the segment corresponding to the greater thickness occupying more than half of said another face, successive adjacent links being mounted head to tail.

6. An endoscope according to claim 5, wherein the holes for passing the cables through the ring-shaped links have conical chamfers to facilitate sliding of the cables.

7. An endoscope comprising:

an ultrasound echography probe having a base and a strip of ultrasound transducer carried by said base;

a manual control housing and manual adjustment members carried by said housing;

a tube fixed to said housing and projecting in a distal direction from said housing;

a mechanical coupler connecting said tube to said base of said probe and controllable by means of the adjustment members, said mechanical coupler comprising a plurality of ring-shaped links mounted in series, of such a shape as to enable each said link to tilt in at least one direction with respect to an adjacent said link, starting from a position in which the coupler is substantially straight;

a plurality of cables connecting said adjustment members and said base, located along and within said tube and said mechanical coupler, said links being held in mutual engagement solely by said cables and at least some of said cables being put under tension by resilient means in said housing;

a plurality of electrical conductors connected to said strip to feed excitation signals to said transducers and to return echo signals therefrom, said electrical conductors being connected to electronic means for delivering said excitation signal of such a nature to cause ultrasonic scanning electronically; and a tubular sleeve of liquid-proof flexible material having one end secured to said base of the probe and another end secured to said housing, said sleeve surrounding said tube and said coupler and being slidably received thereon said sleeve being secured to said base and said housing such that said sleeve is under longitudinal tension when said coupler is substantially straight.

8. An endoscope according to claim 7, wherein each of said links has a flat face and another face made up of two segments parallel to the flat face and interconnected via shoulders parallel to the axis, the segment corresponding to the greater thickness occupying more than half of said another face, successive adjacent links being mounted head to tail.

* * * * *